(12) United States Patent
Abekawa et al.

(10) Patent No.: US 7,153,986 B2
(45) Date of Patent: Dec. 26, 2006

(54) METHOD FOR PRODUCING PROPYLENE OXIDE

(75) Inventors: Hiroaki Abekawa, Toyonaka (JP); Masaru Ishino, Sodegaura (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/506,584

(22) PCT Filed: Feb. 28, 2003

(86) PCT No.: PCT/JP03/02288

§ 371 (c)(1),
(2), (4) Date: Sep. 3, 2004

(87) PCT Pub. No.: WO03/074506

PCT Pub. Date: Sep. 12, 2003

(65) Prior Publication Data

US 2005/0182264 A1    Aug. 18, 2005

(30) Foreign Application Priority Data

Mar. 4, 2002  (JP)  ............................. 2002-056907

(51) Int. Cl.
*C07D 301/02* (2006.01)
*B01J 21/06* (2006.01)

(52) U.S. Cl. ...................... 549/533; 502/350; 549/518; 549/523; 549/524; 549/531

(58) Field of Classification Search ................ 549/533, 549/531, 524, 523, 518; 502/350
See application file for complete search history.

(56) References Cited

U.S. PATENT DOCUMENTS

| 4,833,260 A | 5/1989 | Neri et al. |
| 4,954,325 A | 9/1990 | Rubin et al. |
| 6,106,797 A | 8/2000 | Müller et al. |
| 6,114,551 A | 9/2000 | Levin et al. |

FOREIGN PATENT DOCUMENTS

| EP | 0 100 119 B1 | 9/1986 |
| JP | 4-5028 B2 | 1/1992 |
| WO | WO 03/074421 A1 | 9/2003 |

OTHER PUBLICATIONS

Tatsumi et al., "Hydrothermal Synthesis of a Novel Titanosilicate with MWW Topology", *Chemistry Letters*, pp. 774-775, (2000).
Wu, et al. "Extremely high trans selectivity of Ti-MWW in epoxidation of alkenes with hydrogen peroxide", *Chem. Commun.*, pp. 897-898, (2001).
Shokubai, "Postsynthesis Ti-MWW", *Catalysts & Catalysis*, vol. 44, No. 6, pp. 468-470, (2002).
Clerici et al., "Synthesis of Propylene Oxide from Propylene and Hydrogen Peroxide Catalyzed by Titanium Silicate", *Journal of Catalysis*, vol. 129, pp. 159-167, (1991).
Thangaraj et al., "Catalytic Properties of Crystalline Titanium Silicalites", *Journal of Catalysis*, vol. 130, pp. 1-8, (1991).
Wu et al., "A Novel Titanosilicate with MWW Structure. I. Hydrothermal Synthesis, Elimination of Extraframework Titanium, and Characterizations", *J. Phys. Chem. B*, vol. 105, pp. 2897-2905, (2001).
Report of R&D projects for "Next-generation Chemical Process Technology /Non-halogen Chemical Process Technology" FY2000 Annual Report, pp. 261-168, (2001).
Report of R&D projects for "Next-generation Chemical Process Technology /Non-halogen Chemical Process Technology" FY2001 Annual Report, pp. 168-209, (2002).
"Proceedings of the 88th Catalysis Society of Japan Meeting A", pp. 154, (2001).
"Proceedings of the 89th Catalysis Society of Japan Meeting A", pp. 65, (2002).
Zeolite News Letters, vol. 20 (4), at pp. 147-155, (2003) (partial translation).

*Primary Examiner*—Charanjit S. Aulakh
(74) *Attorney, Agent, or Firm*—Akin Gump Strauss Hauer & Feld, LLP

(57) ABSTRACT

A method is provided for producing propylene oxide, wherein propylene is reacted with hydrogen peroxide in the presence of an organic solvent and a crystalline titanosilicate catalyst having an MWW structure containing Ti, the Ti having been incorporated during crystallization.

5 Claims, No Drawings

METHOD FOR PRODUCING PROPYLENE OXIDE

CROSS-REFERENCE TO RELATED APPLICATIONS

This application is a Section 371 of International Application No. PCT/JP03/002288, filed Feb. 28, 2003, the disclosure of which is incorporated herein by reference.

BACKGROUND OF THE INVENTION

The present invention relates to a process for producing propylene oxide by carrying out an epoxidation reaction of propylene using hydrogen peroxide. More specifically, the invention relates to a process for efficiently producing propylene oxide by performing the reaction using a specific crystalline titanosilicate catalyst having an MWW structure in the presence of an organic solvent.

As the process for producing propylene oxide by carrying out an epoxidation reaction of propylene using hydrogen peroxide, a method of using a TS-1 catalyst (e.g., Japanese Published Examined Application No. 4-5028) is known. The TS-1 catalyst is a crystalline titanosilicate catalyst having MFI structure in accordance with the framework type code of International Zeolite Association (IZA). In addition, when the TS-1 catalyst is used, a methanol solvent is known to be an appropriate solvent (e.g., *Journal of Catalysis* 129:159 (1991)).

Also, as a process for producing propylene oxide by carrying out an epoxidation reaction of propylene with hydrogen peroxide using MWW structure-having crystalline titanosilicate (hereinafter referred to as Ti-MWW) catalyst, there has been a known method that uses a Ti-MWW catalyst, into which titanium (hereinafter referred to as Ti) has been incorporated after crystallization (e.g., U.S. Pat. No. 6,114,551).

Moreover, as a process for producing propylene oxide by carrying out an epoxidation reaction of propylene with hydrogen peroxide, as a medium, using a Ti-MWW catalyst, into which Ti has been incorporated during crystallization, there has been a known method that produces propylene oxide in a water solvent, that is, in an aqueous hydrogen peroxide solution (*Heisei* 12 *nendo Jisedai Kagaku Process Gijutu Kaihatu Non-halogen Kagaku Process Gijutu Kaihatu Seika Houkokusho* (Report of R&D projects for "Next-generation Chemical Process Technology/Non-halogen Chemical Process Technology" FY2000 Annual Report) 261–268, (FY2001)).

However, in the conventionally known production methods, sufficient catalytic activities have not been attained.

BRIEF SUMMARY OF THE INVENTION

The object of the present invention is to provide a process for efficiently producing propylene oxide, which process is a production process of propylene oxide by epoxidizing propylene with hydrogen peroxide.

Thus, the present invention relates to a method for producing propylene oxide, characterized in that it comprises reacting propylene with hydrogen peroxide in the presence of an organic solvent and a crystalline titanosilicate catalyst that has an MWW structure prepared by incorporating Ti during crystallization.

DETAILED DESCRIPTION OF THE INVENTION

The crystalline titanosilicate catalyst having an MWW structure to be used in the present invention is generally known as the Ti-MWW catalyst named from the framework type code of IZA (International Zeolite Association) or the Ti-MCM-22 catalyst.

A generally employed process for producing the crystalline titanosilicate catalyst having an MWW structure is as follows.

A silicon (hereinafter referred to as Si) compound and a Ti compound are hydrolyzed in the presence of a structure directing agent to prepare a gel. A lamellar precursor of crystalline titanosilicate is prepared from the resultant gel by heating in the presence of water (hydrothermal synthesis method or the like). The crystalline titanosilicate catalyst having an MWW structure is prepared by calcination of the lamellar precursor for crystallization.

Alternatively, the crystalline titanosilicate having an MWW structure can also be prepared by conducting a preparation according to the above-described method using a Si compound, and a compound other than Ti, such as an aluminum (hereinafter referred to as Al) compound, or a boron compound, to once prepare, as a precursor, a crystalline metallosilicate having an MWW structure, and subsequently substituting the compound, which was incorporated therein in place of Ti, with Ti.

However, since the pore diameter of a micro-pore structure within a particle of the crystalline titanosilicate catalyst is small in the latter case, it is difficult to incorporate Ti by substitution into the framework within the pore after crystallization. Therefore, in order to incorporate Ti into the framework within the pore by substitution, the layers of the crystal of the crystalline metallosilicate catalyst having an MWW structure once prepared have to be delaminated, thereby collapsing the crystal, and then substituted with Ti, and crystallized again.

With respect to the catalyst to be used in the present invention, it is important to incorporate Ti during crystallization. The incorporation of Ti during the crystallization of Ti-MWW catalyst enables the introduction of Ti into the framework of the pore, thereby the Ti-MWW catalyst that has an MWW structure containing Ti, and which Ti is also present in the pore within the particle can be prepared.

That is, the term "during crystallization" in the present invention stands for "during crystallization of the Ti-MWW catalyst", and does not mean during crystallization of a crystalline metallosilicate catalyst having an element other than Ti formed in the course of preparing the catalyst. Therefore, for instance, a catalyst prepared by delaminating the layers of the crystal of the crystalline metallosilicate catalyst having an MWW structure once prepared, thereby collapsing the crystal, and by subjecting the resulting to substitution with Ti and then crystallization again, is an intended catalyst of the present invention.

Specific examples of the method for preparing the crystalline titanosilicate catalyst that has an MWW structure and contains Ti having been incorporated during crystallization, include the following methods.

Namely, a method of hydrothermal synthesis using titanium alkoxide, described in *Chemistry Letters* 774 (2000), or a method of synthesis using the dry gel conversion method with titanium alkoxide, described in *Proceedings of the* 88*th Catalysis Society of Japan* (*CatSJ*) Meeting A 154 (2000) are known. Alternatively, as described in Shokubai (*Catalysts & Catalysis*) 44(6):468 (2002), the post synthesis process comprising crystallizing, delaminating layers of the resulting crystals, thereby collapsing the crystal, incorporating Ti and then crystallizing again, is a preferred process of preparation because the incorporation of Ti during crystallization enables the incorporation of Ti inside the pore.

In addition, since a Ti-MWW catalyst prepared by using Al, due to the acidity of the residual Al, possibly promotes consecutive reactions of propylene oxide, a preferred Ti-MWW catalyst is one prepared without using an Al compound.

It is known from the disclosure of U.S. Pat. No. 4,954,325 that the MWW structure of the catalyst can be confirmed by X-ray diffraction analysis. in *Chemical Communication* 897 (2001), the results of X-ray diffraction analyses of the crystalline titanosilicate catalyst having an MWW structure are described. Also, it can be confirmed by using ultraviolet and visible spectral analyses as to whether the catalyst is the crystalline titanosilicate catalyst.

In the present invention, reaction is carried out in the presence of an organic solvent. The organic solvents that may be used include organic compounds such as alcohols (methanol, t-butanol, and the like), ketone compounds (acetone, and the like), ether compounds (1,4-dioxane, and the like), ester compounds (methyl acetate, ethyl acetate, and the like), nitrile compounds (acetonitrile, propionitrile, and the like), hydrocarbons (n-heptane, toluene, and the like), halogenated hydrocarbons (1,2-dichloroethane, and the like), and the like. Preferred organic solvents are the nitrile compounds. Among the nitrile compounds, preferred is acetonitrile.

The organic solvent used in the present invention can be used in combination with a compound other than the organic solvents as long as it does not adversely affect the effects of the present invention. Examples of the compound other than organic solvents include water and carbon dioxide. The compound other than organic solvents may be combined with the organic solvent in a liquid state, or combined with the organic solvent in a supercritical state as well.

The ratio of the organic solvent (A) to the compound (B) other than organic solvents ((A)/(B)) is generally 10/90 to 100/0 by weight.

Methods of supplying hydrogen peroxide include a method of supplying a hydrogen peroxide solution prepared in advance, and a method of supplying hydrogen peroxide synthesized in the reaction system. The methods of synthesizing hydrogen peroxide in the reaction system include a method of synthesizing hydrogen peroxide from hydrogen and oxygen, by using a transition metal catalyst, which synthesizes hydrogen peroxide, such as palladium (Pd) or gold (Au), carried or mixed with Ti-MWW catalyst.

When a hydrogen peroxide solution produced in advance is supplied, the hydrogen peroxide concentration in the hydrogen peroxide solution is generally from 0.1 to 70% by weight. In addition, examples of the hydrogen peroxide solution include an aqueous hydrogen peroxide solution or a mixture of hydrogen peroxide solution, water, and the organic solvent.

In the present invention, the epoxidation reaction of propylene with hydrogen peroxide is normally performed at a temperature of 0° C. to 150° C. and normally under a pressure of 0.1 MPa to 20 MPa.

The reaction methods include a fixed bed flow reaction method and a slurry reaction method.

EXAMPLES

Example 1

A reaction was carried out using a Ti-MWW catalyst having a Ti content of 1.1% by weight as determined by ICP emission spectrometry, prepared according to the method described in *Chemistry Letters* 774 (2000). A solution ($H_2O_2$: 5% by weight, water: 47.5% by weight, and acetonitrile: 47.5% by weight) was prepared using a 60% aqueous $H_2O_2$ solution (product of Mitsubishi Gas Chemical), acetonitrile, and purified water. Twelve-grams of the solution thus prepared and 0.010 g of milled Ti-MWW catalyst was loaded into a 50 ml stainless steel autoclave. Then, the autoclave was transferred onto an ice bath and thereinto was loaded 10 g of liquid propylene. Further, it was pressurized to 2 MPa-G with nitrogen. The reaction was deemed started when 5 minutes passed after the autoclave had been placed in hot water bath maintained at 40° C., the inside temperature reaching about 35° C. One hour after the reaction starting, the autoclave was taken out of the hot water bath and sampling was conducted. The pressure at sampling starting was 3 MPa-G. The analysis was carried out by gas chromatography. As a result, the propylene oxide producing activity per unit catalyst weight was 0.463 mol·h$^{-1}$·g$^{-1}$. The propylene oxide selectivity based on propylene was 99.9%.

Example 2

Twelve-grams of the solution prepared by using 0.011 g of the Ti-MWW catalyst used in Example 1, the aqueous $H_2O_2$ solution, acetonitrile and purified water ($H_2O_2$: 5% by weight, water: 47.5% by weight, acetonitrile: 47.5% by weight) and 10 g of liquefied propylene were loaded into an autoclave as in Example 1. It was pressurized to 1 MPa-G with nitrogen, and a catalyst evaluation test was conducted in a similar manner as that of Example 1 at 70° C. using an aluminum block bath in place of a hot water bath. The pressure at sampling starting was 3 MPa-G. As a result, the propylene oxide producing activity per unit catalyst weight was 0.973 mol·h$^{-1}$·g$^{-1}$. The propylene oxide selectivity based on propylene was 98.5%.

Example 3

Twelve-grams of the solution prepared by using 0.010 g of the Ti-MWW catalyst used in Example 1, the aqueous $H_2O_2$ solution, acetone and purified water ($H_2O_2$: 5% by weight, water: 47.5% by weight, acetone: 47.5% by weight) and 10 g of liquefied propylene were loaded into an autoclave as in Example 1. It was pressurized to 2 MPa-G with nitrogen, and a catalyst evaluation test was conducted in a similar manner as that of Example 1 at 40° C. using an aluminum block bath in place of a hot water bath. The pressure at sampling starting was 3 MPa-G. As a result, the propylene oxide producing activity per unit catalyst weight was 0.230 mol·h$^{-1}$·g$^{-1}$. The propylene oxide selectivity based on propylene was 98.4%.

Example 4

A reaction was carried out using a Ti-MWW catalyst having a Ti content of 2% by weight as determined by ICP emission spectrometry, prepared in accordance with the method described in Shokubai (*Catalysts & Catalysis*) 44, 6, 468–470, (2002). Using 12 g of the solution prepared by using 0.010 g of the Ti-MWW catalyst, the aqueous $H_2O_2$ solution, acetonitrile and purified water ($H_2O_2$: 5% by weight, water: 47.5% by weight, acetonitrile: 47.5% by weight) and 10 g of liquefied propylene, a catalyst evaluation test was conducted in the same manner as that of Example 1 at 40° C. using an aluminum block bath in place of a hot water bath. The pressure at sampling starting was 3 MPa-G. As a result, the propylene oxide producing activity per unit catalyst weight was 0.684 mol·h$^{-1}$·g$^{-1}$. The propylene oxide selectivity based on propylene was 99.4%.

Example 5

Twelve-grams of the solution prepared by using 0.010 g of the Ti-MWW catalyst used in Example 1, the aqueous $H_2O_2$ solution, acetonitrile and purified water ($H_2O_2$: 5% by weight, water: 47.5% by weight, acetonitrile: 47.5% by weight) was loaded into a 50 ml stainless steel autoclave. Then, after the air inside the autoclave was replaced by gaseous propylene, the autoclave was transferred onto an aluminum block bath heated in advance to become 40° C., and agitation was started. Concurrently with agitation starting, supplying gaseous propylene adjusted in advance to 0.7 MPa-G with a pressure reducing valve allowed a reaction to start while maintaining the reaction pressure at 0.7 MPa-G. Three hours after the reaction starting, sampling was carried out. As a result, the propylene oxide producing activity per unit catalyst weight was 0.270 mol·h$^{-1}$·g$^{-1}$. The propylene oxide selectivity based on propylene was 99.6%.

Example 6

Twelve-grams of the solution prepared by using 0.010 g of the Ti-MWW catalyst used in Example 1, the aqueous $H_2O_2$ solution, propionitrile and purified water ($H_2O_2$: 5% by weight, water: 47.5% by weight, propionitrile: 47.5% by weight) and 10 g of liquefied propylene were loaded into an autoclave as in Example 1. It was pressurized to 2 MPa-G with nitrogen, and a catalyst evaluation test was conducted in the same manner as that of Example 1 at 40° C. using an aluminum block bath in place of a hot water bath. The pressure at sampling starting was 3 MPa-G. As a result, the propylene oxide producing activity per unit catalyst weight was 0.370 mol·h$^{-1}$·g$^{-1}$. Compounds derived from propylene detected by gas chromatography were only propylene oxide, and by-products such as propylene glycol were not detected.

Example 7

Twelve-grams of the solution prepared by using 0.010 g of the Ti-MWW catalyst used in Example 1, the aqueous $H_2O_2$ solution, 1,2-dichloroethane and purified water ($H_2O_2$: 5% by weight, water: 47.5% by weight, 1,2-dichloroethane: 47.5% by weight) and 10 g of liquefied propylene were loaded into an autoclave as in Example 1. It was pressurized to 2 MPa-G with nitrogen, and a catalyst evaluation test was conducted in the same manner as that of Example 1 at 40° C. using an aluminum block bath in place of a hot water bath. The pressure at sampling starting was 3 MPa-G. As a result, the propylene oxide producing activity per unit catalyst weight was 0.273 mol·h$^{-1}$·g$^{-1}$. The propylene oxide selectivity based on propylene was 97.3%.

Example 8

Twelve-grams of the solution prepared by using 0.010 g of the Ti-MWW catalyst used in Example 1, the aqueous $H_2O_2$ solution, toluene and purified water ($H_2O_2$: 5% by weight, water: 47.5% by weight, toluene: 47.5% by weight) and 10 g of liquefied propylene were loaded into an autoclave as in Example 1. It was pressurized to 2 MPa-G with nitrogen, and a catalyst evaluation test was conducted in a similar manner as that of Example 1 at 40° C. using an aluminum block bath in place of a hot water bath. The pressure at sampling starting was 3 MPa-G. As a result, the propylene oxide producing activity per unit catalyst weight was 0.290 mol·h$^{-1}$·g$^{-1}$. The propylene oxide selectivity based on propylene was 98.0%.

Comparative Example 1

A reaction was carried out in a similar manner as the method of Example 1 with the exception that a TS-1 catalyst having a Ti content of 1.3% by weight as determined by ICP emission spectrometry, prepared in accordance with the method described in *Journal of Catalysis* 130:1 (1991) was used and that methanol was used instead of acetonitrile. The propylene oxide producing activity per unit catalyst weight was 0.165 mol·h$^{-1}$·g$^{-1}$. The propylene oxide selectivity based on propylene was 95.8%.

Comparative Example 2

A catalyst evaluation test was conducted in a similar manner as that of Example 4 by use of 12 g of the solution prepared by using 0.010 g of the Ti-MWW catalyst used in Example 1, the aqueous $H_2O_2$ solution, and purified water ($H_2O_2$: 5% by weight, water: 95% by weight) and gaseous propylene adjusted to 0.7 MPa-G with a pressure reducing valve. As a result of analyzing the product after three hours from the reaction starting, the propylene oxide producing activity per unit catalyst weight was 0.057 mol·h$^{-1}$·g$^{-1}$. The propylene oxide selectivity based on propylene was 86.8%.

INDUSTRIAL APPLICATION

As detailed thus far, according to the present invention there can be provided a process for efficiently producing propylene oxide by reacting hydrogen peroxide with propylene in the presence of a crystalline titanosilicate catalyst having an MWW structure and of an organic solvent.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for producing propylene oxide, comprising reacting propylene with hydrogen peroxide in the presence of an organic solvent and a crystalline titanosilicate catalyst, wherein the catalyst has an MWW structure containing Ti, the Ti having been incorporated during crystallization of the crystalline titanosilicate catalyst.

2. The method according to claim 1, wherein the organic solvent is a nitrile compound.

3. The method according to claim 1, wherein the crystalline titanosilicate catalyst having an MWW structure is prepared without using aluminum.

4. The method according to claim 1, wherein hydrogen peroxide used in the reaction is synthesized within the reaction of propylene.

5. The method according to claim 1, wherein the crystalline titanosilicate catalyst is prepared by providing a crystalline metallosilicate catalyst having an MWW structure and having layers, delaminating the layers of the crystalline metallosilicate catalyst such that the crystallinity of the metallosilicate catalyst is collapsed, and subjecting the collapsed catalyst to substitution with titanium and crystallization to form the crystalline titanosilicate catalyst.

* * * * *